United States Patent
Zañartu Salas et al.

(10) Patent No.: US 10,783,630 B2
(45) Date of Patent: Sep. 22, 2020

(54) METHOD FOR ESTIMATING FORCE AND PRESSURE OF COLLISION IN VOCAL CORDS FROM HIGH-SPEED LARYNGEAL VIDEOS

(71) Applicant: UNIVERSIDAD TECNICA FEDERICO SANTA MARIA, Valparaiso (CL)

(72) Inventors: Matías Zañartu Salas, Vina del Mar (CL); Manuel Esteban Diaz Cadiz, Santiago (CL)

(73) Assignee: UNIVERSIDAD TECNICA FEDERICO SANTA MARIA, Valparaiso (CL)

(*) Notice: Subject to any disclaimer, the term of this patent is extended or adjusted under 35 U.S.C. 154(b) by 68 days.

(21) Appl. No.: 16/247,099

(22) Filed: Jan. 14, 2019

(65) Prior Publication Data
US 2019/0147593 A1 May 16, 2019

Related U.S. Application Data

(63) Continuation-in-part of application No. PCT/CL2016/050037, filed on Jul. 14, 2016.

(51) Int. Cl.
*G06T 7/00* (2017.01)
*G06T 7/13* (2017.01)
(Continued)

(52) U.S. Cl.
CPC ........ *G06T 7/0012* (2013.01); *A61B 1/00009* (2013.01); *A61B 1/267* (2013.01);
(Continued)

(58) Field of Classification Search
CPC ............... G06T 7/0012; G06T 7/13; G06T 2207/30004; G06K 9/00; A61B 1/00009; A61B 1/267; A61B 1/2673
See application file for complete search history.

(56) References Cited

U.S. PATENT DOCUMENTS 3,925,616 A * 12/1975 Sondhi ................. A61B 1/2673
   704/201
2002/0184009 A1* 12/2002 Heikkinen .......... G10L 19/0204
   704/219
(Continued)

OTHER PUBLICATIONS

Powell, The Efficacy of Laryngeal Imaging to Assess the Effect of Vocal Fold Masses on Vibratory Function, 2015, (Doctoral dissertation, University of Cincinnati, 151 pages (Year: 2015).*
(Continued)

*Primary Examiner* — David F Dunphy
(74) *Attorney, Agent, or Firm* — Elmore Patent Law Group, P.C.; Joseph C. Zucchero; Carolyn S. Elmore

(57) ABSTRACT

The present invention relates to a collision force analysis (CFA) method for obtaining in vivoestimates of contact force and pressure in the vocal cords directly from laryngeal videoendoscopies. The method comprises the steps of: providing at least a high-speed laryngeal videoendoscopy (also called High Speed Videoendoscopy or HSV) to generate at least one image and videos of the vocal cords; pre-processing the image in a processing unit, to define a region of interest (ROI) of the location of the glottis; detecting in the processing unit, the edges of the vocal folds in the images obtained by means of the HSV; recording in the processing unit, the points of the edges detected by means of a sequence of images; estimating in the processing unit, the path of the vocal cord edge during collision throughout time; and estimating the values of contact and impact of the vocal cords by means of a collision model.

12 Claims, 5 Drawing Sheets

(51) Int. Cl.
*A61B 1/267* (2006.01)
*A61B 1/00* (2006.01)
*G06K 9/00* (2006.01)

(52) U.S. Cl.
CPC .............. *A61B 1/2673* (2013.01); *G06K 9/00* (2013.01); *G06T 7/13* (2017.01); *G06T 2207/30004* (2013.01)

(56) References Cited

U.S. PATENT DOCUMENTS

2008/0300867 A1\* 12/2008 Yan .................... G10L 25/48
  704/207
2011/0299748 A1  12/2011 Nishimura et al.

OTHER PUBLICATIONS

Gunter, H.E. Mechanical Stresses in Vocal Fold Tissue During Voice Production (2003). Retrieved from the Internet <URL: www.biorobotics.harvard.edu/pubs/hgthesis.pdf>.

\* cited by examiner

METHOD FOR ESTIMATING FORCE AND PRESSURE OF COLLISION IN VOCAL CORDS FROM HIGH-SPEED LARYNGEAL VIDEOS

FIELD OF APPLICATION

The present invention relates to a method of extracting and analyzing clinical information associated with the vibration occurring in the vocal cords from an examination of laryngeal videoendoscopy. The objective of the method proposed is to estimate the force and collision pressure experienced by the vocal cords during the glottal closing periods.

BACKGROUND

Voice is a phenomenon caused by the coordinated action between the respiratory system, the larynx and the nasal and voice cavities. At the time of speech, it is often necessary to supplement these structures to generate sound by the sustained vibration of the vocal cords, a process known as phonation. The study of voice is closely related to the extraction, estimate and analysis of relevant medical parameters during these phonatory processes. The evaluation of the speech function is clinically examined by considering the aerodynamic, acoustic and mechanical components involved in the process of speech in patients, the laryngeal inspection being the most direct medical examination for studying the voice function and their possible disorders. In most cases, the vocal disorders are due to a malfunction or improper use of the vocal cords. These abuses are recurrent when the voice is forced by speaking, singing, crying, coughing or by exposing the larynx to irritating substances, reflux or cigarettes. The most common disorders of the vocal cords are laryngitis, vocal nodes, polyps, and vocal paralysis. Laryngtis is an inflammation of the vocal cords that is perceived as a rough or hoarse voice. It can be caused by excessive use of voice, reflux, infections, or irritating agents. The vocal nodes are benign growths on the vocal cords produced by voice abuse; they are small and generally grow in pairs. They are normally formed in areas where the vocal cords repeatedly receive most of the pressure when hitting and causing the voice to become hoarse, low and cracking. It is a typical problem of singers, teachers or professional speakers. A polyp (Reinke's edema or polypoid degeneration) is a soft growth similar to a blister that normally grows only on a vocal cord. It is often produced by the long use of tobacco, although other causes may be hypothyroidism, reflux or a continuous improper use of the voice. The vocal polyps cause the voice to be hoarse, low, and cracking. The paralysis in the vocal cords is a loss of the motor control of the larynx which prevents the folds from opening or closing properly; this may occur in one or both vocal cords. A person suffering from paralysis may have difficulty when swallowing and/or coughing.

In particular, the mechanism involved in the development of the nodes as a speech alteration is primarily dysphonia. Dysphonia is a term used to refer to voice disturbances when it differs to the point of calling attention with respect to other people of the same gender, similar age and cultural group, comparing intensity, tone, volume and flexibility of diction.

When the alteration is extreme, it can produce cases of Aphonia, which corresponds to the total loss of voice. There are two large classifications, functional or organic dysphonia.

Functional dysphonia, also known as muscular tension dysphonia (MTD) is an alteration of the voice in the absence of any neurological or structural disease of the larynx. They are usually associated with excessive contractions of the laryngeal musculature or defects in the glotic closure, showing a hyperfunctional voice (also called phonotraumatic voice). This type of dysphonia is externally manifested by the fast depletion of pulmonary air, gasping and excessive muscle contraction. While many alterations are initially functional, when the long term speech abuse is sustained, the persistence of the symptoms results in physical lesions (from inflammations to the appearance of polyps or nodules) and the problem turns into an organic dysphonia, i.e. involving an anatomical or structural alteration. Therefore, these alterations can be commonly strengthenes each other through a cause and effect behavior, generating hyperphonation cycles, appearance of lesions, functional reinforcement and worsening of the lesion.

Laryngeal inspection is a medical examination that allows the vocal cords to be directly viewed by a tube (which may be rigid or flexible) whereby a light is sent and due to its optical images of the interior of the larynx can be obtained. One end of this is introduced by the mouth (rigid endoscope) or by nasally (flexible endoscope) and the other end can be inspected by the eye of the professional or be coupled to a camera in order to record the examination. We refer to these recordings under the name of laryngeal videoendoscopy.

The use of endoscopic instrumentation with standard cameras is currently quite common in laryngoscopy examinations. Stroboscopic techniques in these acquisition systems have allowed the study of the vocal folds during the phonation cycle without necessarily requiring high sampling frequencies, since the speed of vibration reaching the vocal cords is above the common frame rate in video recordings (Between 150 to 300 [Hz] of fundamental frequency of vibration, compared with the 30 fps of a standard video).

Basically, the stroboscopic principle is the capture of images with intermittent illumination at a slightly deviated refresh rate (a fraction) of the fundamental frequency of vibration of the cords, causing an aliasing effect that allows reconstructing an apparent oscillation sequence of the vocal cords from several real oscillation cycles. These systems function quite well as long as patients studied maintain a sustained and symmetrical phonation regimen. Pathological cases with asymmetric vibrations or irregular patterns represent a problem for stroscopic systems, since the representativeness of the oscillations is lost. This limitation may be a problem when studying the development of lesions in the tissue when the synchronization thereof in phonation is not good.

High speed recording systems for these laryngoscopy examinations are a relatively recent technological development and which have allowed the capture of a greater amount of phenomena that occur in the glottis compared to stroboscopic techniques. These examinations provide greater temporal resolution, which is useful for capturing the kinematic of the vocal folds in both normal and pathological cases during phonatory periods, or also the start and end thereof. These irregularities can now be observable, but it is stated that many of the criteria used by the laryngeal stroboscopy cannot be used for abnormal vibrations, and that there is no precise and reliable scoring method for these cases. Therefore, the analysis could eventually end only based on the experience of the examiner.

The evaluation of the laryngeal examinations in practice is largely subjective, directly depending on the judgment of the specialist and subject to perceptual criteria in its diagnosis. Common perceptual criteria are described in the state of the art, where the quality of the diagnosis is comparatively explored between stroboscopic examinations and high speed glotography. In these experiments data is inspected visually only under a protocol of degrees rates and scales assigned, such as the quality of the glottgal closure, the amplitude of the fold, quality of the mucous wave, type of phonation appreciated, etc. Current studies disclose that evaluations performed with high speed glotography showed fewer non evaluable cases and less frequent methodological failures, in addition to a lower percentage of disagreement between evaluators. However, it is noted that the perceptual evaluations have a wide variability in diagnosis and that objective methods of analysis are necessary. None of these amounts was directly related to the stress or degree of abuse experienced by the vocal folds.

A more objective representation method corresponds to a technique called video-chemography, which consists in capturing a crosssection of the speech fold in the video, agglomerating the captured lines over time one after another, forming a single image called the chemogram. With this, the evaluation of oscillation irregularities is possible as well as tone interruptions, delay in the onset of vibration, asymmetries, etc. The analysis of the chemogram is typically visual and takes into account only a crosssection of the glottis.

Recent works with the use of chemography to extract metrics and perform quantitative analyses can be observed in relatively new studies. In these studies, glottic closure coefficients and symmetry metrics are calculated by chemoographic results and compared with a digital voice production model, establishing that the assymetries found relate to changes in the modulation of the air flow.

Another representation of the phonatory cycle developed is the phonovibrogram, which consists in a viewing technique that separates the vocal folds and generates a temporary space map of the deflection of each fold with respect to a medial axis. This representation includes facilities for differentiating different vocal records according to the geometrical shape aopted by the representation for each case.

In general, various edge extraction techniques, segmentation and glottal recording are currently used by various studies to extract speech parameters from endoscopic videos. Clear examples of these methods are: parameterization of the glottal area, segmentation of glottgal edges, representation of the glottis deflection in other spaces in order to measure asymmetries in vibration, or even segmentation of lower and upper folds by depth estimate. In other studies, the speech folds are also analyzed with classification techniques, so that to separate vocal records from dysphonic versus non-dysphonic patients, thus pre-determining a set of glottal parameters (such as a glottal area, width, length, etc.).

The etiology of organic pathologies in the vocal folds, such as nodes and polyps, has been widely associated with an increase in the collision forces on the vocal cords. The damages experienced by the membranous tissue produce in medial sectors of the glottis during the collision phases under conditions of extended and/or inadequate phonation; thus the shock pressure is expected to be maximum at these points. Despite the great interest existing for directly evaluating these collisions, their in vivo quantification has been very difficult and it has not been included in clinical examinations, since only a few studies have been able to gather data on the collision pressure directly on people. This is why other approaches have been considered to investigate the collision, in order to understand its relationship with the development of lesions. Under these approaches numerical simulations are included, as well as measurements on larynxes removed from animals, and physical replicas of voice cords made from silicone.

Direct in vivo measurements of the collision force with probes and experimental configuration on human vocal cords have been successfully made. The collision magnitudes obtained are within a range of 13 to 210 [mN] and a large correlation between peak of collision strength and voice intensity was found. Although the probe exhibits adaptation capabilities for use in humans (with high temporal resolution and low noise level) the measurements are sensitive to the placement of the sensor and the technique is basically invasive. In vivo collision pressure data were also combined in a previous study, where the collision at the midpoint of the vocal cord is reported from 0.5 to 3.0 [kPa]. Due to experimental limitations, only 7 of the 20 subjects were analyzable. Another similar research showed that intraglottal collision pressures in 20 patients ranged from 1 to 4 [kPa], and that the larger values were found in subjects with lesions near the placement of the probe. In all of these examinations, topical anesthesia was required on the tissue prior to insertion of the probe.

Intraglottal pressure has also been measured directly on larynxes removed from canines. In this case, it has been observed that the impact instants of vocal cords produce sharp collision pressure pulses, which are positively related to the induced subglottic pressure, the maximum elongation of the tissue reached and the adduction of vocal cords (due to the posture and muscular activation of the larynx).

Numerical approaches with finite element models (FEM) have been used to evaluate the role of the collision forces as a risk factor in the development of benign lesions. The study found that the elastic forces within the vocal tissue dominate the lock mechanics in the vocal cord and that there is a relationship between the subglottic pressure and the maximum collision force, as already stated in experimental measurements. Studies suggest that the collision rebound is not sufficient to produce the glottal opening and that aerodynamic forces dominate the spacing of the cords after the impact. In addition, the mechanical forces result in a glottal closure and are responsible for the magnitude of the impact.

Physical replicas have also been used to study the collision of speech folds. In this case, the collision forces are obtained using the Hertz impact model. Stroscopic systems and high speed cameras are used to record the surface of the replica while being subjected to forced phonation, and the Digital Image Correlation (DIC) method is applied to quantify the distribution of tension on the upper surface. The Hertz estimate requires this voltage analysis to calculate its predictions according to a depth or penetration parameter obtained through an extrapolation on the strain values obtained by the method.

DIC is shown as a potential indirect estimator of the collision stress, but it can be biased, because the damage of the vocal tissue due to the impact occurs inside the tissue and not on the upper surface, where the deformation variations are calculated. Therefore, this approach is susceptible to overestimating the collision forces. In addition, DIC would require a secure way to generate a pattern of small dots on the vocal tissue for applying this method in vivo to a patient, which is not yet resolved.

One of the important points to note is that the methods described are not well suited to be applied to clinical conditions. Direct measurements are basically invasive and indirect measurements using DIC still require the intervention of the tissue with visible marks on the surface, which tends to be complicated when considering live human subjects. However, these studies report that the Hertzian collision model may be useful to estimate collision stresses. The use of this model shows advantages over direct measurement methods, since it avoids the intervention of the patient's glottis. The problem is that it needs a penetration parameter, obtained with DIC to operate, and, in addition, there is no way of drawing a pattern of points on the tissue under usual clinical conditions. Thus, potential methods that allow this parameter to be obtained, avoiding the calculation of the deformation map of the tissue, are desirable in order to apply the Hertz model to the clinical context.

The study of voice production requires multidiscipline approaches to understand the phonation process. This involves mechanical, acoustic and aerodynamic interactions between the tissue and the air flow. Obtaining clinical data related to these components is very important in order to establish a good evaluation of the voice function.

Various acoustic metrics are commonly used for the evaluation of voice, such as Sound Level Pressure, SPL, fundamental frequency, jitter (percentage variation of the fundamental frequency), shimmer (percent variation of the sound level), Harmonic-to-noise-ratio H/N, etc. These parameters are obtained from the audio recordings, and are therefore the simplest to calculate. However, several of these acoustic parameters are unconclusive at the time of evaluating the origin of a speech alteration by themselves, since the deviation of these may be due to several factors.

Aerodynamic metrics are somewhat more difficult to extract directly, but there are techniques for determining their values from the flow and oral pressure, by a Rothenmberg mask. Preset vocal exercises are requested to the patient in order to be recorded with an acquisition system and then processed. From these data, the subglottal pressure is estimated, as well as the Maximum Phonation Time, MPT, the glottal air flow, the Maximum Flow Declination Rate, MFDR, the continuous component of air flow (DC Flow), etc. Studies have established correlations of some of these values with "acystic" parameters, with significant differences between patients being reported.

However, mechanical metrics with respect to the physical collision between the vocal tissues are the most complex to obtain and require direct inspection of the vocal cords, or even relatively invasive interventions with force or pressure sensors are necessary for a respective evaluation. There is not a standard clinical parameter for determining the behaviour of the impact of the vocal tissue, but a hypothesis has been suggested regarding the role of the collision of the vocal cords in the generation of pathologies and organic lesions associated with a sustained vocal abuse, which has not yet been clinically studied or validated in human subjects in the long term. The most direct clinical procedure for evaluating voice production in a patient is a laryngeal endoscopy. Recently, the incorporation of new technology in the medical instrumentation has enabled the laryngoscopy examinations to be provided with video acquisition capability, allowing the observation of a variety of vibratory phenomena occurring within the larynx. There are two types of acquisition systems used in these examinations: the stroboscopic systems and the high-speed acquisition systems. These developments have incorporated the potential of providing new information about the vibratory patterns, both in normal and pathological cases, where the tones are usually unstable and exhibit irregular vibratory movements. Particularly interesting phenomena in the visual study of the vocal cords are the shock profile of the vocal cords and the propagation waves on the mucous tissue during each cycle.

Finding objective methods to improve the clinical analyses of these examinations is critical at this point, since obtaining detailed information on the kinematics of the vocal cords allows the study of the mechanical behaviour thereof.

Solutions of this type have been stated by the state of the art. For example, the US 2005219376 document describes an image recording device, preferably an image printing color device with recording modes for examinations of the voice cords. In one embodiment of the invention, the document describes that the recording device comprises an endoscope for the mapping of the vocal cords.

Another similar solution is that disclosed by US 2008300867 document, which refers to a method for obtaining a quantitative measure of the voice comprising the use of a recording selected from types of recording comprising a recording of laryngeal images and an acoustic recording. In one embodiment of the invention, the behaviour of the vocal cords is measured by a high speed endoscope video (HSV).

WO2014148712 relates to a videochemography system for analyzing the state of movement of the mucosa of the vocal cords. The system comprises: a laryngoscope for viewing the vocal cords; a light source for illuminating the vocal cords; a video camera for recording and storing images observed through the laryngoscope; a computer incorporating an image capture unit for the conversion of a video signal transmitted from the video camera into a digital image signal, a storage unit for storing the digital image signal, a control unit for analyzing the image signal of the storage unit and displaying the results of the analysis on a monitor, and an analysis software for the analysis of the image signal of the storage unit; and a monitor for the visualization of an analysis of the image and results and capture.

Technical Problem

The potential of video-larynxgoscopy has not been exploited in studying the process of lesions development in the vocal cords, regardless of the relevant visual information in these examinations. Typically, cases of greater occurrence and interest are phonotraumatic organic lesions like nodes or polyps, for which it is important to determine early risk factors and possible development of these lesions in the clinic. It is presumed that the main problem with these videos is to extract objective information about the potential damage suffered by the tissue in scenarios of improper vocal stress. This behavior is usually observed under an endoscopic examination where some vocal exercises proposed by a specialist or phonoaudiologist are performed, and then a subjective observation of these phenomena, establishing possible degrees of abuse and/or bad vocal technique by the visual appreciation of the glottic closure, periodicity and phase asymmetries and amplitude. While the patient's tracking can be effective, early signs of the development of a problem or injury are difficult to identify under this frame, and in general, require the examiner's skill to determine such degrees.

The main challenge with these recordings is to evaluate the vibratory information observed and then performing a more accurate early clinical diagnosis. Commonly, this evaluation is subject to the specialist's subjective judgment, based on only perceptual protocols, scales, or criteria. It should be also mentioned that at times the objective of the examination is only the inspection, because it is carried out when the patient has already generated the clinical symptoms and it is used as direct evidence of a problem not timely controlled. Under this point of view, the main problem in question is the lack of objective criteria for the evaluation of vocal abuse recorded in laryngeal endoscopies, which may potentially give clues about some future problem or condition in the voice. But the problem remains about how to quantitatively measure the stress experienced by the tissue from a video-laryngoscopy, and if from these data a more comprehensive knowledge can be obtained on the condition of the vocal folds in a patient.

Technical Solution

In order to solve these problems, a method for obtaining in vivo estimates is proposed of the force and pressure of collision in the vocal cords directly from laryngeal videoendoscopies. It is believed that the apparent penetration and the collision area can be approximatedly obtained by using only the kinematic information observed in these recordings, which would then allow the prediction of the force and collision pressure by the Hertz model.

The present invention further comprises a method for the processing of video which allows this task to be performed.

This method allows supplementing the clinical study of the phonotraumatic dysphonia with objective information and that these indirect estimates are simple enough to be applied in contexts where the videoendoscopic examination is available.

DETAILED DESCRIPTION OF THE INVENTION

Figure 1:
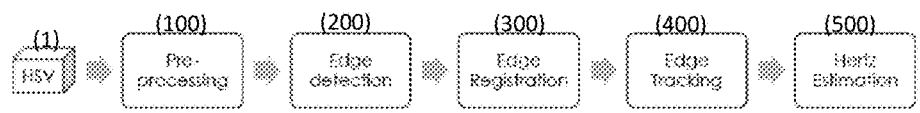
FIG. 1 corresponds to a block diagram with the steps of the collision force analysis method, according to an embodiment of the invention.

The present invention relates to a method for the Collision Force Analysis or CFA. Said method comprises at least 5 steps, as shown in FIG. 1.

First, at least one High Speed Laryngoscopy (1) (referred to as High Speed Videoendoscopy or HSV) is presented as input to the method, so that to generate at least one image and videos of vocal cords (2). Thereafter, the images and videos are sent to a processing unit (not shown in the figures), wherein a pre-processing step (100) is applied to correct the orientation of the glottis, defining a region of interest (ROI) in its location. Then, edge detection (200) is performed on the vocal folds, which is processed by a sequence of operators (300) which analyzes the gradient information in the image. The location of each edge (2a, 2b) of the vocal cord (right and left) is segmented and a polynomial adjustment is applied to record the set of points found for each edge (2a, 2b). The recorded coefficients are provided to a Kalman filter that provides an estimate of the path of the vocal edge during the collision over time (400), or tracking. A mass-spring model is used to follow the edge trajectory during the collision phase. Finally, the penetration or overlap values between the edges and the contact section between them are extracted to calculate the impact estimates through the Hertzian (500) model.

During the pre processing step (100) of the videos obtained through HSV (1) there is a correction of the rotation of the endoscopic image by the user comprised, which is carried out by selecting the anterior and posterior endpoints in the glottis to establish the necessary angle for compensation. A reference image of the sequence during glottic closure is used to view these points. The user then defines a region of interest (ROI) and a $M_{ROI}$ mask centered on the glottis to establish what section of the video will be processed. Typically, a HSV recording has undesired low frequency movements related to the usual manipulation of the endoscope. A motion compensation algorithm is pre applied to the video in the event that "cleaning" the low frequency movements present is necessary, this being why the location of the ROI can be considered fixed and not requiring updating.

Figure 2:
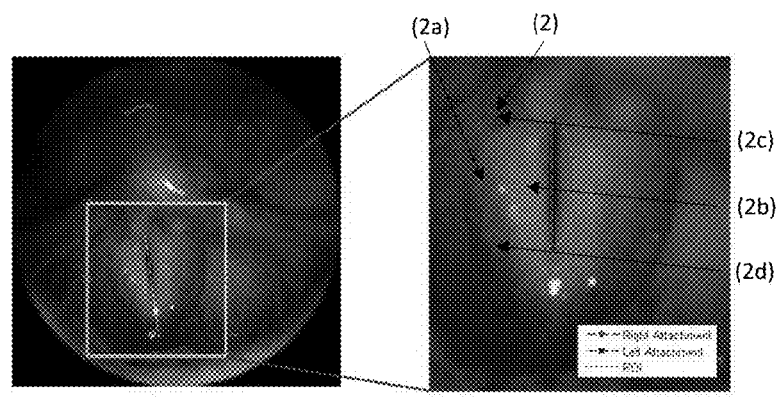
FIG. 2 corresponds to an image of a vocal cord with their respective edges and predefined attachment points, according to an embodiment of the invention.

Additionally, a pair of points on each vocal cord are defined by user input, which are referred to attachment points (2c, 2d), which are referenced as $(x_a; y_a)$ and $(x_b; y_b)$. As noted in FIG. 2, these attachment points (2c, 2d) define where the resting positions of the folds observed in the video are found, assuming a straight line between them as the central location of the oscillation of each tissue during phonation. Under this assumption, these attachment points (2c, 2d) are considered close to the glottis endpoints (both anterior and posterior) under complete closing of the glottis. However, these points (2c, 2d) may differ from this respective glottal midline (a line formed by the joining of the anterior or posterior spaces of the glottal area) especially in the cases of patients with incomplete glottal closure. When contact between tissues is partial, an opening appears at the back of the glottis, which induces a more distant location of these upper attachment points by the user. For CFA, the attachment points are necessary to "grip" a curve representing the vocal edge. These are constraints for a problem of polynomial adjustment used to represent each fold.

In the step of detection (200), the HSV passes through a sequence of the basic image processing operations by the processing unit. Each frame I is converted into a grey scale image $I_g$ and a morphological reconstruction operation is applied on its reverse to clean the specular reflection generated by the mucosa of the vocal cords. Next, a Prewitt operator is applied to obtain the magnitude and phase of the gradient, $G_A$ and $G_\phi$ (in degrees) respectively. $G_A$ is masked with the $M_{ROI}$ obtained in the previous stage ($G=GA \cdot M_{ROI}$) and used to segment the edges, separating G into two gradient images as follows:

$$G_{right}(x, y) = \begin{cases} G(x, y)B_r(x, y) & G(x, y) > t_h, \\ 0 & i.o.c. \end{cases} \quad (1)$$

$$G_{left}(x, y) = \begin{cases} G(x, y)B_l(x, y) & G(x, y) > t_h, \\ 0 & i.o.c. \end{cases} \quad (2)$$

$$B_r(x, y) = \begin{cases} 1 & G_\phi(x, y) > 90 \lor G_\phi(x, y) < -90, \\ 0 & i.o.c. \end{cases} \quad (3)$$

$$B_l(x, y) = \begin{cases} 1 & G_\phi(x, y) < 90 \lor G_\phi(x, y) > -90, \\ 0 & i.o.c. \end{cases} \quad (4)$$

where $t_h$ is a threshold parameter. From these gradient images $G_{right}$ y $G_{left}$, the location of the edge is calculated on axis x for each horizontal line of the ROI, forming pairs is calculated (x; y) of points located in the centroid of the gradient found:

$$(\bar{x}_j, \bar{y}_j) = \left( \frac{\sum_{i=1}^{w} i \cdot G_s(i, j)}{\sum_{i=1}^{w} G_s(i, j)}, j \right) \quad (5)$$

$\forall j \in [1, h]$, $s \in [\text{left}, \text{right}]$. Where w and h are respectively the width and height of the ROI. Only up to the endpoints of glottis are taken into account. The upper and lower points outside the range defined by the attachment points are omitted. Finally, a temporary average mobile filter is applied at each $\bar{X}_j$ position the invention in order to obtain a smooth variation of the fold movement, reducing the detection error in the local position of the edge.

$$(x_j, y_j)_k = \left( \left[ \frac{1}{N} \sum_{i=-\lfloor(N-1)/2\rfloor}^{\lfloor(N-1)/2\rfloor} \bar{x}_{j,k-i} \right], \bar{y}_{j,k} \right) \quad (6)$$

Figure 3:
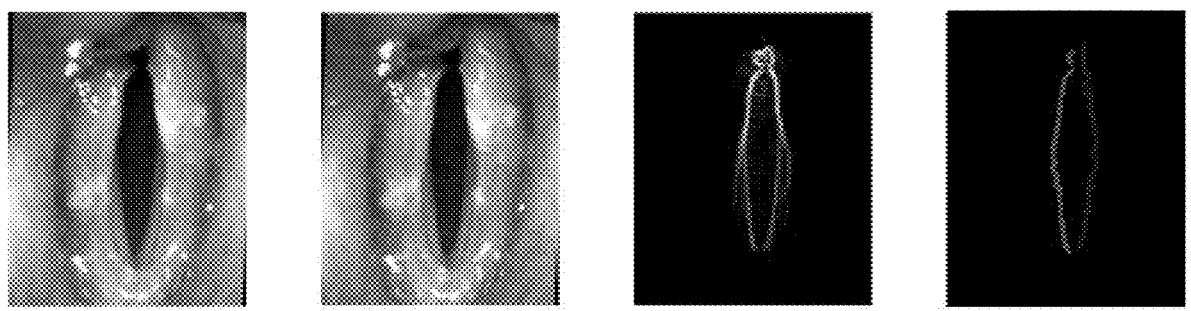
FIG. 3 corresponds to an image of a vocal cord in the step of detecting vocal edges, according to an embodiment of the invention.
Figure 4:
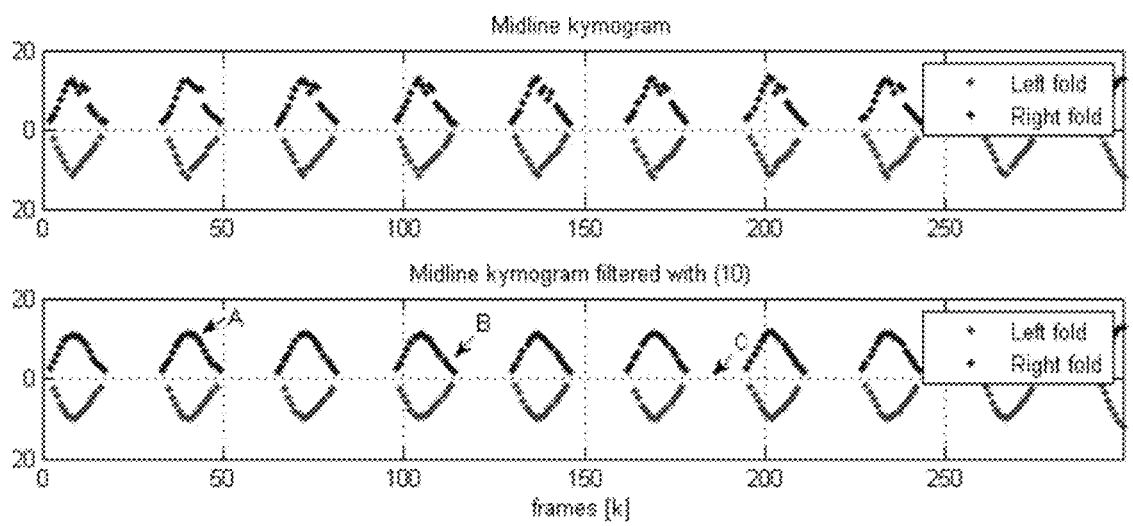
FIG. 4 corresponds to a temporal representation of the detection step, according to an embodiment of the invention.

$\forall k \in [1, N_{frames}]$, wherein N=5. In FIG. 3, an example is shown of this detection step applied on a HSV recording only as example and in FIG. 4 a temporary representation of the medial portion of the glottis with a chemogram is seen. As it can be seen, the gradient information is used to find the left and right vocal edges, but the detected points are lost when the flods collide each other (time C in the temporary sequence of FIG. 4). The smoothing performed by the temporary filter reduces the detection error during the glottal opening and closing phase, but when the impact starts, the gradient does not exceed the $t_h$ threshold set and the edge location is lost. The task of the following steps will be to establishing a framework allowing estimating the projection of these edges during the times of impact.

In the recording step (300), conducted on the processing unit, the points (x; y) found in the detection step (200) are used to adjust a polynomial of the p order by applying the Least Squares (LS) estimator to the detected points along a line (or coordinate axis) defined by the attachment points $(x_a; y_a)$ y $(x_b; y_b)$. The points of attachment are taken into account as fixed roots of the solution, thereby determining constraints to the problem. The M polynomial to be adjusted when the line of attachment is vertical ($x0=xa=xb$) is defined as:

$$M_p(y) = \quad (7)$$

$$ay^p + by^{p-1} + cy^{p-2} + dy^{p-3} + \ldots = \left( \sum_{i=0}^{p-2} \theta_i y^i \right)(y - y_a)(y - y_b) + x_0$$

Wherein the coefficients of the M polynomial written are in general as follows:

$$\Phi = (a \ b \ c \ d \ \ldots)^T \quad (8)$$

The value of these coefficients is constrained by the roots $y_a$ y $y_b$. By factoring these constraints on M, the unknown parameters of the curve to be adjusted can be cleared, said set being defined as:

$$\Phi = \theta \odot (1 - (y_a + y_b) y_a y_b)^T \quad (9)$$

If the attachment points do not define a vertically oriented line, rotating all of the set of points detected is previously required to view the problem from the coordinate axis determined by these restrictive points. If the angle of inclination of this line is φ, then the points detected in the new coordinate system can be obtained with the following transformation:

$$\begin{pmatrix} u \\ v \end{pmatrix} = \begin{pmatrix} \cos\varphi & -\sin\varphi \\ \sin\varphi & \cos\varphi \end{pmatrix} \begin{pmatrix} x \\ y \end{pmatrix} \quad (10)$$

And the M curve to be adjusted is rewritten as:

$$M_p(v) = (\Sigma_{i=0}^{p-2} \theta_i v^i)(v - v_a)(v - v_b) + u_0 \quad (11)$$

With this, the LS solution used to compute the θ parameters in equation 1 corresponds to:

$$\theta = (A^T A)^{-1} A^T U \quad (12)$$

$$A = \begin{pmatrix} \tilde{v}_1 v_1^{p-2} & \ldots & \tilde{v}_1 v_1 & \tilde{v}_1 \\ \tilde{v}_2 v_2^{p-2} & \ldots & \tilde{v}_2 v_2 & \tilde{v}_2 \\ \vdots & \ddots & & \vdots \\ \tilde{v}_D v_D^{p-2} & \ldots & \tilde{v}_D v_D^{p-2} & \tilde{v}_D \end{pmatrix}$$

$$U = \begin{pmatrix} \tilde{u}_1 \\ \tilde{u}_2 \\ \vdots \\ \tilde{u}_D \end{pmatrix}$$

$$\tilde{u}_l = u_l - u_0 \quad (13)$$
$$\tilde{u}_l = (v_l - v_a)(v_l - v_b)$$
$$\forall l \in [1, D]$$

Where the pairs $(u_l; v_l)$ are the points obtained in the detection step with the equation (6) and previously transformed with equation (10), and D is the number of points found in the detection step. This regression is applied for each set of points of vocal cords, both left and right, and after being applying to the equation 12, their values $\theta_k$ are recorded along the sequence of the video.

In this step, also the rate of change of the coefficients ($\dot{\Theta}_k$) is estimated:

$$\dot{\Theta}_k = \frac{1}{\Delta t}(\Theta_k - \Theta_{k-1}) \quad (14)$$

Figure 5:
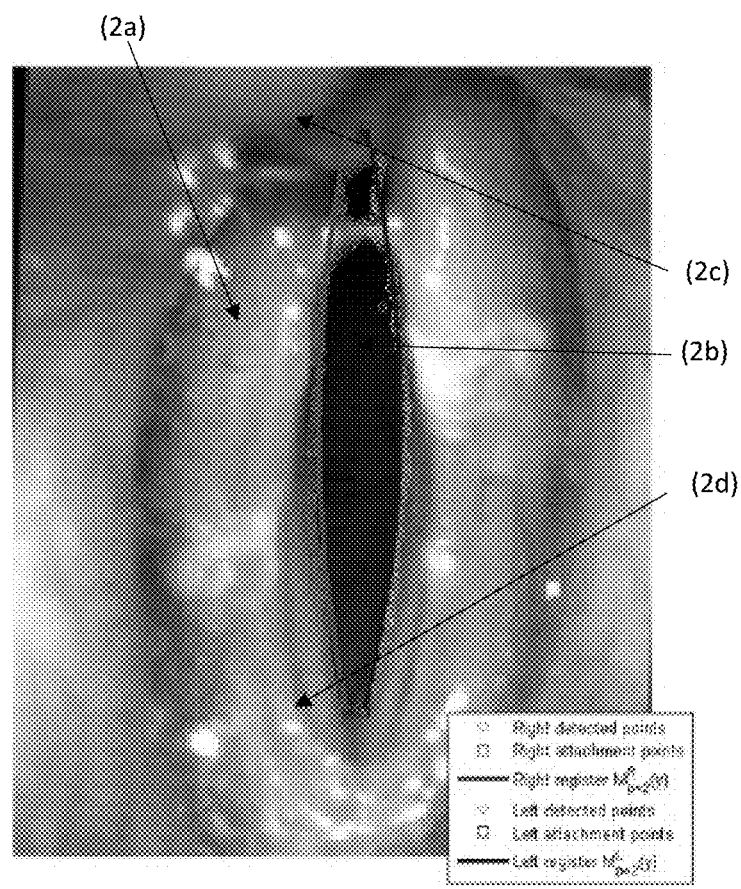
FIG. 5 corresponds to an image of the recording stage of the vocal cords, according to an embodiment of the invention.

Both the value or location of the coefficients $\Theta_k$ and their respective velocities $\dot{\Theta}_k$ are the input records to the next tracking stage. These values are considered as observations of a process describing the dominant oscillating mode of the vocal folds. The recording process can be seen in FIGS. 5 and 6.

Figure 6:
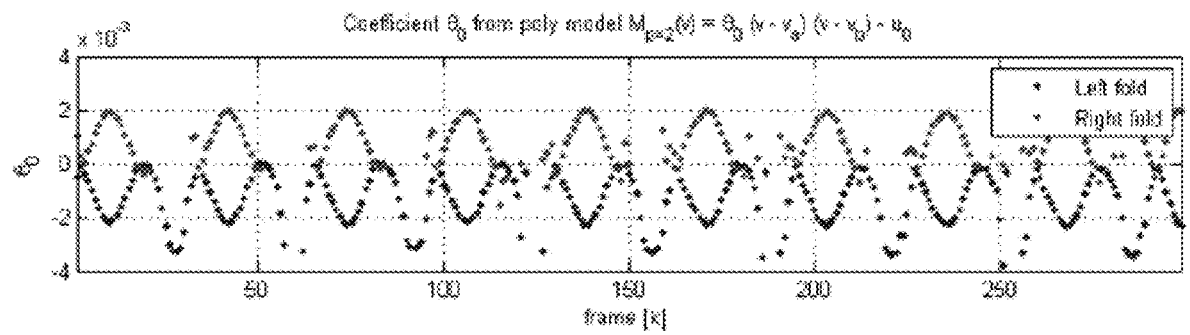
FIG. 6 corresponds to a temporary representation of the recording step, according to an embodiment of the invention.

As can be seen in FIG. 6, the values of $\Theta_k$ tend to show poor adjustment solutions during the collision phases of the tissue. This is basically because the least squares estimate is not well conditioned when the amount of detected points D suddenly decreases, which occurs by the reach of the $t_h$ gradient threshold in the detection step. At this point, the values of the record obtained during the collision are invalid and do not represent useful information during the impact. Thereby, they can be regarded as an occlusion problem of the vocal edge, whose handling will be performed in the next follow-up step (400).

In the tracking step (400) the occlusion of the vocal cords is regarded as a problem of estimating the status variables in the presence of noise and data loss. Here a Kalman filter is applied to perform predictions on the value and rate of change that the $\Theta$ coefficients should have over the contact period. In order to describe these occlusion periods with a linear process, it is assumed that the main mode of vibration in the vocal cords can be represented by a mass-spring configuration, that is, a pair of springs fixed in their respective attachment lines (defined in the pre processing stage (100)).

Under this assumption, the model used to describe the vibratory process of a vocal cord corresponds to:

$$X_{i,k+1} = AX_{i,k} + V_k \quad (15)$$

$$Y_{i,k} = CX_{i,k} + E_k \quad (16)$$

$$Y_{i,k} = \begin{pmatrix} \theta_{i,k} \\ \dot{\theta}_{i,k} \end{pmatrix}$$

$$A = \begin{pmatrix} 1 & \Delta t \\ -k\Delta t & 1-b\Delta t \end{pmatrix}$$

$$C = \begin{pmatrix} 1 & 0 \\ 0 & 1 \end{pmatrix}$$

Where $X_{i,k}$ is the particular state of the coefficient $\theta_i$ in $\Theta_k$ at time k, $Y_{i,k}$ are observations of the state of the process, which we assume as available with matrix C as identity. $V_k$ an $E_k$ are the processing noise and measurement noise, cConsidered Gaussian and noncorrelated with variances $\sigma_v$ and $\sigma_e$ respectively. $\Delta t = 1/f_s$ is the sampling time, k the stiffness of the spring, and b the damping value of the process. The "mass" of the coefficient is not present, since the interest lies in representing the kinematic of the vocal edge and this only translates into a scaling factor for the solution. Therefore, the mMass parameter will be considered as unit in this process. Tuning this process to a particular $w_r$ resonance is sought, which enables to describe the path of $\Theta_k$ during the occlusion. Thus, $w_r$ and $\xi$ are defined as cControl parameters for the dynamic response of the process.

$$k = \frac{w_r^2}{1-\xi^2} \quad b = 2\xi\sqrt{k} \quad (17)$$

The parameter $\xi$ is thought only to avoid possible unstable solutions and low values near zero are usually considered (0-0.03). This offsets possible instabilities of the process due to discretization of the system (high values of K are prone to generate poles slightly outside of the unit circle). The stiffness k is automatically calculated by estimating the resonance frequency $w_r$, using the kinematic information from the recording stage.

Figure 7:
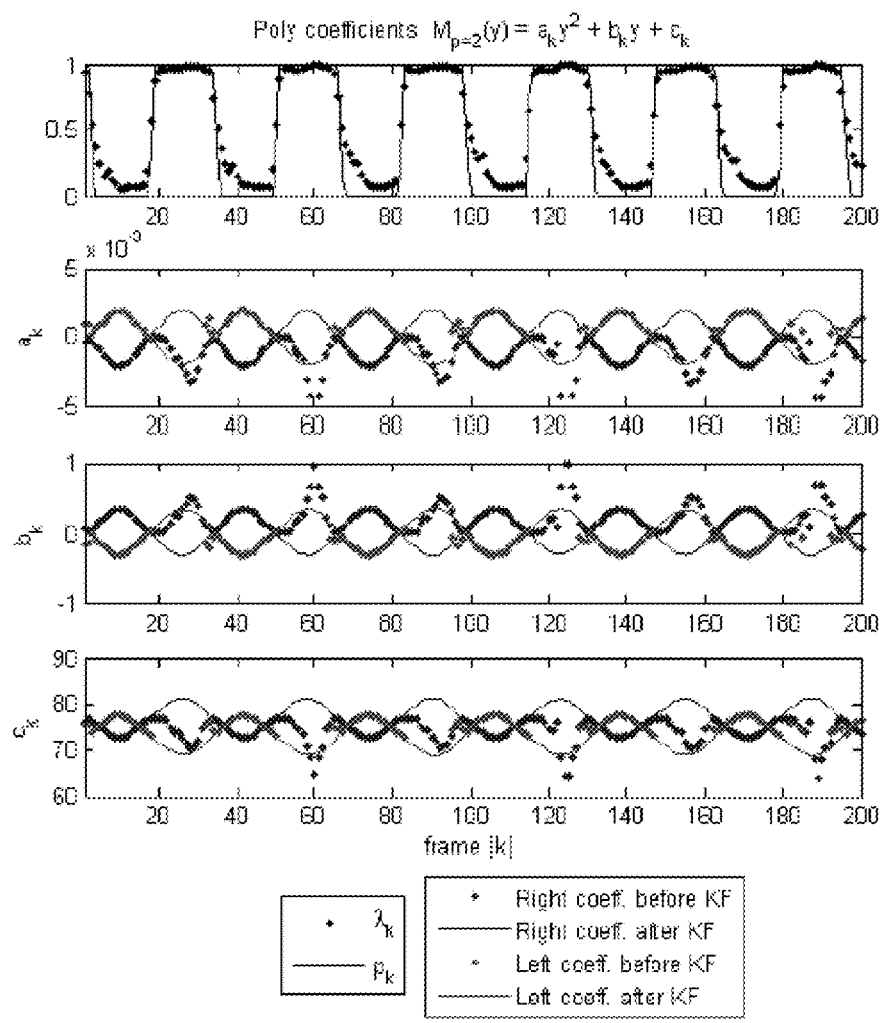
FIG. 7 corresponds to an estimate of coefficients during the collision at the tracking stage, according to an embodiment of the invention.

For establishing the resonance value, the analytical solution of the mass-spring model is considered at initial conditions as a target function of a minimization problem. The values of $\theta_{i,k_0}$ and $\dot{\theta}_{i,k_0}$ are considered at $k_0$ previous time to the impact as initial condition values, so that the analytical solution of the mass-spring model for these conditions coincides with a similar position of return, but at the end of the contact at $k_1$ time. Thereby to determine a value of $w_r$ meeting the following is interesting:

$$w_r = \operatorname*{argmin}_{w} \| F_{i,k_1}(w) - \theta_{i,k_1} \| \quad (18)$$

$$F_{i,k_1}(w) = \theta_{i,k_0}\cos(wt_{k_1}) + \frac{\dot{\theta}_{i,k_0}}{w}\sin(wt_{k_1}) \quad (19)$$

Where $t_{k_1} = (k_1 - k_0)\Delta t$. As can be seen in FIG. 7, the solution of equation 18 is not necessarily unique and the method of resolution thereof may fall into local minimums. However, it is expected that the target resonance frequency is maintained close to the fundamental frequency executed by the patient during recording. In a preferred embodiment of the invention, the resolution method used is a standard Nelder-Mead and its starting condition is set to an expected fundamental frequency of oscillation in the order of 200 [Hz].

This $w_r$ resonance value controls the necessary k stiffness for the process to synchronize a simple harmonic motion on the temporal evolution of each vocal cord, but it is only intended to complete the sequence during the collision times. When the vocal edges are visible, there is no priority for the use of the process for the estimation of the trajectory, since there is no occlusion. In order to define when the process predictions will be required, the following amounts are defined:

$$\lambda_K = \frac{D_T - D_k}{D_T} \quad \rho_k = \frac{1}{1 + e^{-\beta(\lambda_K - \gamma)}} \quad (20)$$

which are respectively referred to as the ratio of undetected points $\lambda_K$ and its associated uncertainty factor $\rho_k$. $D_T$ represents the maximum possible amount of points detected at the edge, $D_k$ the current amount of detected points, $\beta$ a gain factor, and $\gamma$ an uncertainty threshold. The uncertainty factor determines how much "mistrust" we have on recorded values of $\Theta_k$. When $D_k$ is very small, for example, $\lambda_k$ increases above the uncertainty threshold and $\rho_k$ tends to unity, which means that there are many points lost in the detection step and the adjustment of the polynomial in the recording step is bad. This indicator states that the estimates of the Kalman filter are necessary in such a circumstance and require higher priority. The following equations describe the implementation of the Kalman filter developed (the indices of i coefficients are omitted for simplicity):

$$\hat{X}_{k+1|k} = A\hat{X}_{k|k} \quad (21)$$

$$\hat{X}_{k|k} = (I - J_k C)\hat{X}_{k|k-1} + J_k \bar{Y}_k \quad (22)$$

$$J_k = P_{k|k-1}C^T[CP_{k|k-1}C^T + P_E]^{-1} \quad (23)$$

$$P_{k+1|k}=AP_{k|k}A^TP_V \quad (24)$$

$$P_{k|k}=P_{k|k-1}(1-\rho_k)J_kCP_{k|k-1} \quad (25)$$

$$\hat{Y}_k=C\hat{X}_{k|k-1} \quad (26)$$

Kalman considers this uncertainty factor $\rho_k$ as a quantifier of the degree of mistrust or loss of kinematic information in the observation. This is internally controlled by modifying the $J_k$ gain matrix of the filter, adjusting the weight of the second term in the equation (25) which updates the covariance of the estimate error $P_{k|k}$.

The output estimate is defined as $\overline{Y}_k$, which is a linear combination between the $Y_k$ observations of the status obtained in the recording step and the predictions made of the $\hat{Y}_k$ status.

$$\overline{Y}_k=(1-\rho_k)Y_k+\rho_k\hat{Y}_k \quad (27)$$

It should be noted that by controlling the $\rho_k$ factor, the filter selects the best set of available coefficients to represent the curve describing the vocal fold. Finally, the first value of the $\overline{Y}_k$ vectors (the value estimated of the position of the coefficient $\theta_{i,k}$) is grouped into a $\overline{\Theta}_k$ vector and then by the expression (9) the resulting $\overline{\Phi}_k$ coefficient vector is calculated for the final representation of the edge.

Figure 8:
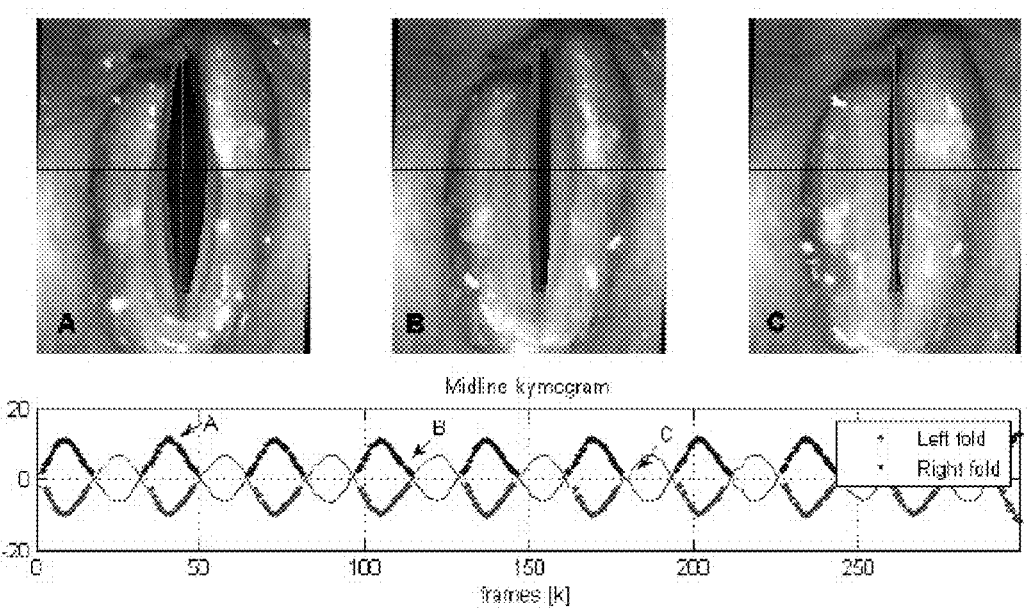
FIG. 8 corresponds to a temporary representation of the tracking step according to an embodiment of the invention.

In the example illustrated in FIG. 7, the response of the filter against changes in uncertainty in the variation of the recorded coefficients can be observed. The filter handles the loss of points detected by increasing $\rho_k$ and switches to the internal predictions of these values if necessary. The last position and speed achieved at the previous time of the impact is taken into consideration to previously estimate the k parameter of the process. During the collision, the Kalman filter continues the sequence with the predictions, ignoring the values of misconditioned coefficients. When the collision is terminated and the occlusion of the vocal fold is no longer a problem, the estimate returns to the edges previously detected in the previous step. This allows for the complete representation of the entire cycle, which is possible to note in FIG. 8. By gently completing the temporary evolution of vibration of each vocal cord, regardless of the deformation thereof at the moment of impacting, the apparent penetration $\delta_k$ between the overlapping cords is now visible and can be used to estimate the collision of the tissue.

In the step of estimating the contact (500), carried out at the processing unit, the apparent $\delta_k$ penetration is drawn between the tissues and the contact section $\alpha_c$ from the previously estimated trajectory. The difference between the left and right polynomials evaluated at their respective $\overline{\Phi}_k$ coefficients is used to compute this pair of values as follows:

$$\Delta\hat{x}_{j,k}=M_p(y_{i,k};\overline{\Phi}_k^{left})-M_p(y_{j,k};\overline{\Phi}_k^{right}) \quad (28)$$

$$\delta_k=\eta\cdot m\acute{a}x\{\Delta\hat{x}_{j,k},\forall_j\} \quad (29)$$

$$\alpha_k=\eta\cdot\Sigma\forall j\{\Delta\hat{x}_{j,k}>0\} \quad (30)$$

Figure 9:
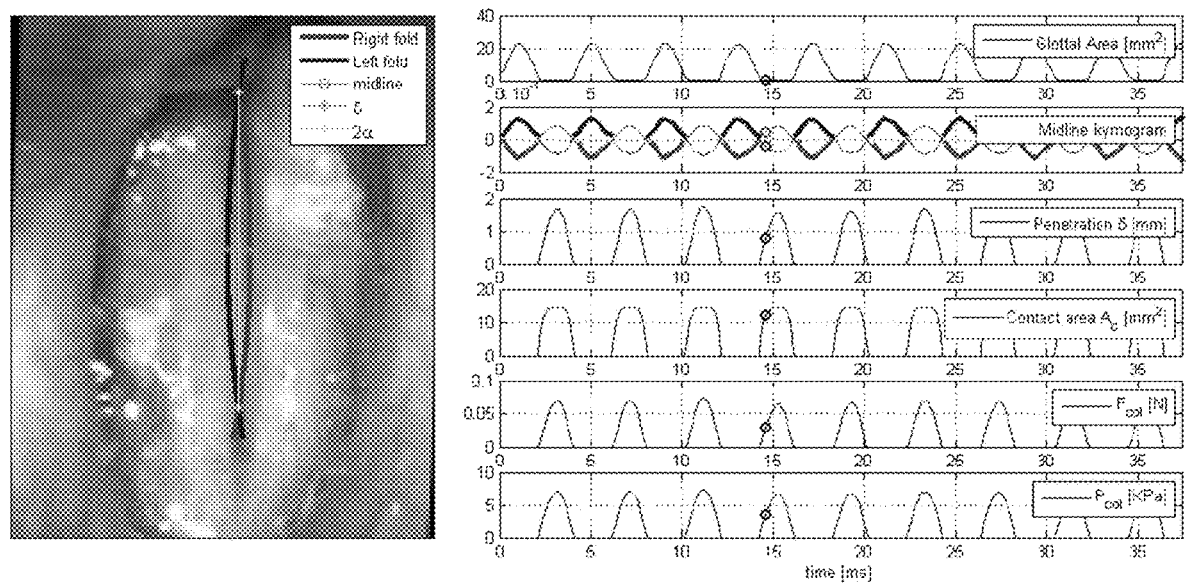
FIG. 9 corresponds to the step of estimating the collision in the vocal cords, according to an embodiment of the invention.

The $\eta$ gain is a video calibration factor to turn the spatial dimension of pixels into meters, which will be assumed to be known. Finally, the penetration and degree of contact are evaluated in the Hertzian contact equations to obtain the predictions of force and pressure of contact suffered by the tissue displayed on a HSV recording to be analyzed, as shown in FIG. 9. In this example, the values of force and pressure are only suggested since the parameters, T, L, $\eta$ and E* used herein are not calibrated for this case.

For the cylindrical contact it is fulfilled with $$P_c = 4E^*\alpha\frac{\delta_c}{L_c}.$$

Where $\delta c$ is the penetration, Lc is the length of the contact, $\alpha$=1.679 is a correction factor and E* is the effective Young modulus define by $$E^* = \frac{E}{2(1-v^2)}.$$

Figure 10:
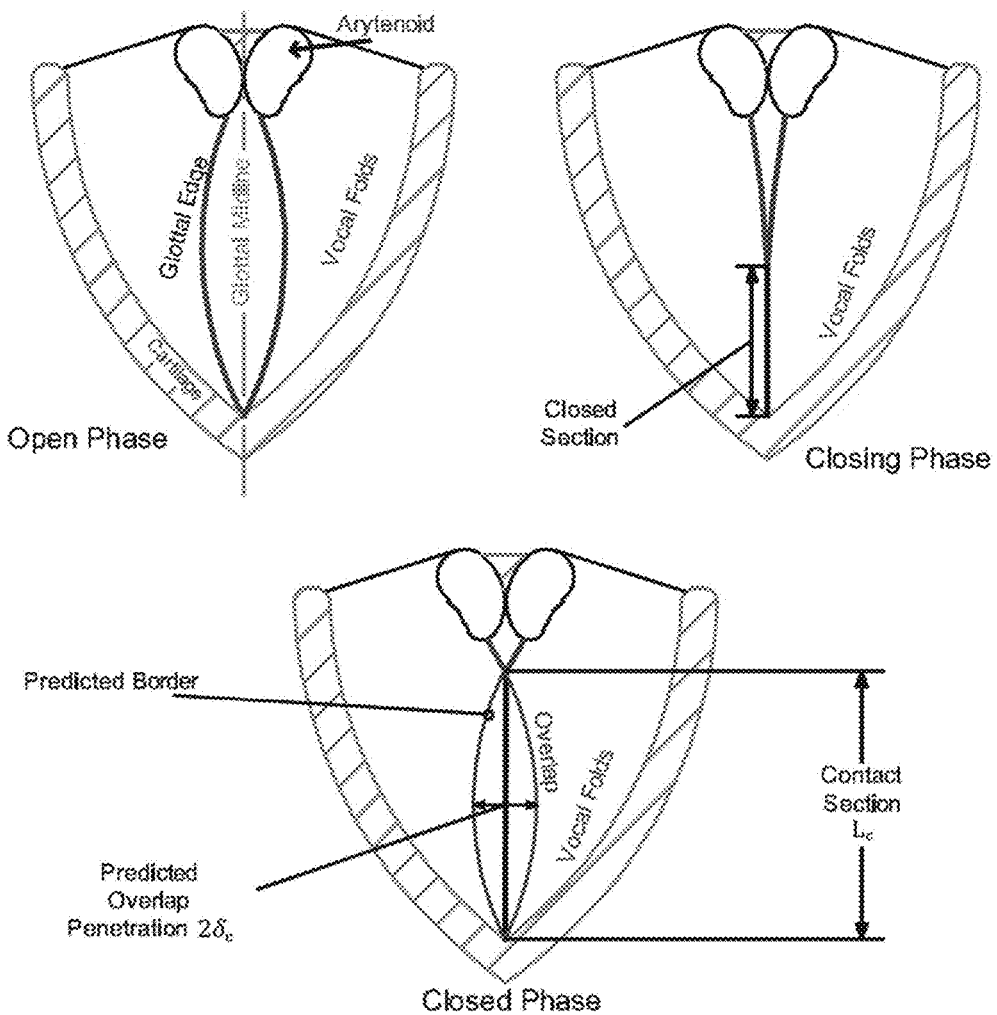
FIG. 10 corresponds to an outline of a sequence of movement of the vocal cords in a typical videoendoscopy recording.

Outline of a sequence of movement of the vocal cords in a typical videoendoscopy recording is shown in FIG. 10. The colored lines represent the estimation of the edge of each vocal fold (left in red, right in blue). The superposition of fictitious edges during the collision shows the estimated depth of penetration (delta_c) and contact length (L_c).

The invention claimed is:

1. A method of analysis of collision force or CFA to obtain in vivo estimates of force and contact pressure on the vocal cords directly from laryngeal videoendomates, CHARACTERISED in that it comprises the steps of:
    a. providing at least high-speed laryngeal videoendoscopy (also called High Speed Videoendoscopy or HSV) to generate at least one image and videos of the vocal cords;
    b. pre-processing the image in a processing unit, to define a region of interest (ROI) of the location of the glottis;
    c. detecting in said processing unit, the edges on the vocal cords in the images obtained by means of the HSV;
    d. recording in said processing unit, the detected points of the edges by means of a sequence of images;
    e. estimating in said processing unit, the path of the vocal cord edge during collision throughout time; and
    f. estimating the values of contact and impact of the vocal cords by means of a contact model.

2. The method according to claim 1, CHARACTERIZED in that in the step of recording the edges, the location of each edge of the vocal cord is segmented and a polynomial adjustment is applied to record the set of points found for each edge.

3. The method according to claim 1, CHARACTERIZED in that to detect the path according to the detected points of the edges, a Kalman filter is used.

4. The method according to claim 1, CHARACTERIZED in that the contact model is a Hertzian model used to calculate impact estimates from penetration or overlapping values between the edges.

5. The method according to claim 1, CHARACTERIZED in that the pre processing step comprises a correction of the rotation of the endoscopic image by selecting the anterior and posterior endpoints in the glottis to establish the necessary angle of compensation.

6. The method according to claim 5, CHARACTERIZED in that in the pre processing step at least a pair of attachment points is defined, which in turn define where the resting positions of the folds observed in the video.

7. The method according to claim 1, CHARACTERIZED in that in the detection step the left and right vocal edges are determined from the gradient images of the vocal cords.

8. The method according to claim 1, CHARACTERIZED in that in the recording step, the points found in the detection step are used to adjust a p order polynomial by applying a least squares estimator (LS) over the detected points.

9. The method according to claim 3, CHARACTERIZED in that the Kalman filter is applied to perform predictions on the value and rate of change that the positions should have along the contact period.

10. The method according to claim 9, CHARACTERIZED in that the main mode of vibration of the vocal cords may be represented by a mass spring configuration.

11. The method according to claim 1, CHARACTERIZED in that in the step of estimating the contact, the apparent penetration between the tissues and the contact section is extracted from the path previously estimated.

12. The method according to claim 1, CHARACTERIZED in that in the step of estimating the contact, the penetration and degree of contact are evaluated in the Hertzian contact equations in order to obtain the predictions of contact force and pressure suffered by the tissue displayed on a HSV recording to be analyzed.

* * * * *